United States Patent
Cull et al.

(10) Patent No.: US 11,830,340 B1
(45) Date of Patent: Nov. 28, 2023

(54) METHOD AND SYSTEM FOR SECRETION ANALYSIS EMBEDDED IN A GARMENT

(71) Applicant: Davinci Wearables, LLC, Concord, MA (US)

(72) Inventors: Christy Fernandez Cull, Cambridge, MA (US); Maria Galou Laymeyer, Cambridge, MA (US); Manisha Mohan, Cambridge, MA (US)

(73) Assignee: Davinci Wearables, LLC, Concord, MA (US)

( * ) Notice: Subject to any disclaimer, the term of this patent is extended or adjusted under 35 U.S.C. 154(b) by 0 days.

(21) Appl. No.: 18/072,509

(22) Filed: Nov. 30, 2022

Related U.S. Application Data

(60) Provisional application No. 63/354,070, filed on Jun. 21, 2022.

(51) Int. Cl.
| | | |
|---|---|---|
| *G08B 23/00* | (2006.01) | |
| *G08B 21/18* | (2006.01) | |
| *A61B 5/00* | (2006.01) | |
| *A61B 5/117* | (2016.01) | |
| *A61B 10/00* | (2006.01) | |
| *A61B 5/11* | (2006.01) | |

(Continued)

(52) U.S. Cl.
CPC .............. *G08B 21/18* (2013.01); *A61B 5/117* (2013.01); *A61B 5/1112* (2013.01); *A61B 5/6804* (2013.01); *A61B 5/746* (2013.01); *A61B 10/0045* (2013.01); *D03D 1/0088* (2013.01); *D03D 15/533* (2021.01); *D10B 2501/00* (2013.01); *D10B 2509/00* (2013.01)

(58) Field of Classification Search
CPC ....... G08B 21/18; A61B 5/1112; A61B 5/117; A61B 5/6804; A61B 5/746; A61B 10/0045; D03D 1/0088; D03D 15/533; D10B 2501/00; D10B 2509/00
See application file for complete search history.

(56) References Cited

U.S. PATENT DOCUMENTS 6,365,417 B1 *  4/2002  Fleming ........... G01N 33/54388
                                                             435/7.1
9,142,839 B2 *  9/2015  Revol Cavalier ..... H01M 6/045
(Continued)

FOREIGN PATENT DOCUMENTS

| CN | 109640820 A | * | 4/2019 | ......... A41D 13/1281 |
| GB | 2585817 A | * | 1/2021 | ........... A61B 5/6808 |
| WO | WO-2011038310 A1 | * | 3/2011 | ......... A61B 1/00016 |

*Primary Examiner* — Toan N Pham
(74) *Attorney, Agent, or Firm* — Caldwell Intellectual Property Law, LLC

(57) ABSTRACT

An apparatus, and method, for a garment embedded secretion analysis. The system includes a liner that includes at least a sensor from a plurality of sensors. The system also includes a computing device embedded in the liner and communicatively connected to the at least a sensor, where the computing device includes a detection module configured to extract at least a biological sample from the user, authenticate the user as a function of the biological sample and a biological data of the user, detect a condition datum as a function of the biological sample and biological data of the user and determine an event datum as a function of the condition datum. Computing device also includes a safety module configured to receive the event datum and generate an alert datum as a function of the event datum.

20 Claims, 12 Drawing Sheets

(51) Int. Cl.
    *D03D 1/00*           (2006.01)
    *D03D 15/533*      (2021.01)

(56) References Cited

U.S. PATENT DOCUMENTS

| | | | | |
|---|---|---|---|---|
| 10,037,672 | B1 * | 7/2018 | Abraham | A61B 5/02055 |
| 10,115,291 | B2 * | 10/2018 | Tallent | A61F 13/42 |
| 10,950,340 | B2 * | 3/2021 | Ranta | G08B 21/20 |
| 2007/0270774 | A1 * | 11/2007 | Bergman | G16H 40/60 |
| | | | | 604/361 |
| 2019/0069827 | A1 * | 3/2019 | Davies | A41B 9/04 |

\* cited by examiner

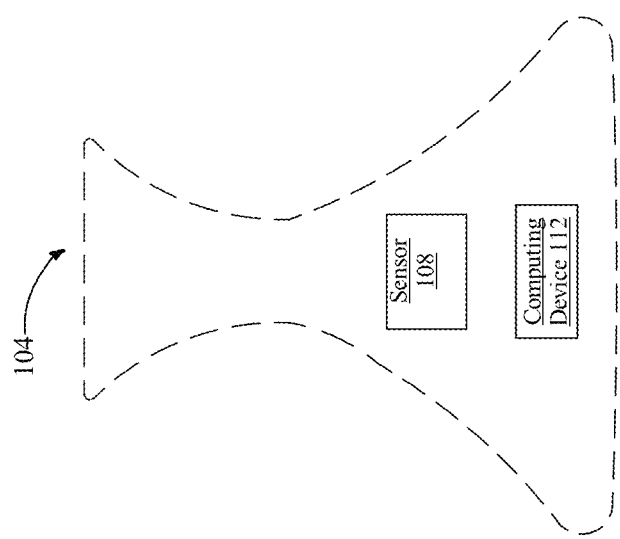

METHOD AND SYSTEM FOR SECRETION ANALYSIS EMBEDDED IN A GARMENT

CROSS-REFERENCE TO RELATED APPLICATIONS

This application claims the benefit of priority of U.S. Provisional Patent Application Ser. No. 63/354,070, filed on Jun. 21, 2022, and titled "A SMART UNDERWEAR GARMENT SYSTEM," which is incorporated by reference herein in its entirety.

FIELD OF THE INVENTION

The present invention generally relates to the field of secretion analysis. In particular, the present invention is directed to monitoring safety and health of a user through a device embedded in garment.

BACKGROUND

Smart technology in clothing garments can help alleviate harm as well as regulate the body of a person. Smart technology in clothing may help to prevent future harm through detection of harmful elements in person's body and alerting the user of the presence of the harm.

SUMMARY OF THE DISCLOSURE

In an aspect an apparatus for a garment embedded secretion analysis. The apparatus including a liner that includes at least a sensor from a plurality of sensors. The system also includes a computing device embedded in the liner and communicatively connected to the at least a sensor, where the computing device includes a detection module configured to extract at least a biological sample from the user, authenticate the user as a function of the biological sample and a biological data of the user, detect a condition datum as a function of the biological sample and biological data of the user and determine an event datum as a function of the condition datum. Computing device also includes a safety module configured to receive the event datum and generate an alert datum as a function of the event datum.

In another aspect a method for a garment embedded secretion analysis. The method includes extracting, by a computing device communicatively connected to at least a sensor embedded in a liner, at least a biological sample from a user. The method also includes authenticating, by the computing device, the user as a function of the at least a biological sample and biological data of the user, and detecting, by the computing device, a condition datum as a function of the biological sample and biological data of the user. The method also includes determining, by the computing device, an event datum as a function of the condition datum and generating, by the computing device, an alert datum as a function of the event datum.

In another aspect a method of manufacturing a garment embedded secretion analysis system. The method of manufacturing includes collecting a fabric to comprise a liner for the garment, weaving conductive yarn into the fabric of the liner, embedding at least a sensor from a plurality of sensors into the fabric of the liner, and installing a computing device into the liner.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 2D is an exemplary embodiment of a liner;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for garment embedded secretion analysis system. In an embodiment, a computing device includes a detection module that extracts a biological sample from a user, authenticate the user based on the biological sample and biological data of the user, detects a condition datum based on the biological sample and biological data of the user, and determine an event datum based on the condition datum. The computing devices also includes a safety module that receives the event datum from detection module and generates an alert datum based on the event datum.

Aspects of the present disclosure can be used to monitoring fertility of a user. Aspects of the present disclosure can also be used to alert user and others of the presence of dangerous elements in user's body, such as elements known as rape drugs. This is so, at least in part, because system is configured to detect the presence of the element in a biological sample, determine that this element is a specific rape-drug and generate an alerting warning user and others of the possible involuntary intoxication, which may enable user to seek help and other to help the user.

Aspects of the present disclosure allow for transmitting a user's location, based on GPS, when danger is detected. Exemplary embodiments illustrating aspects of the present disclosure are described below in the context of several specific examples.

Figure 1:
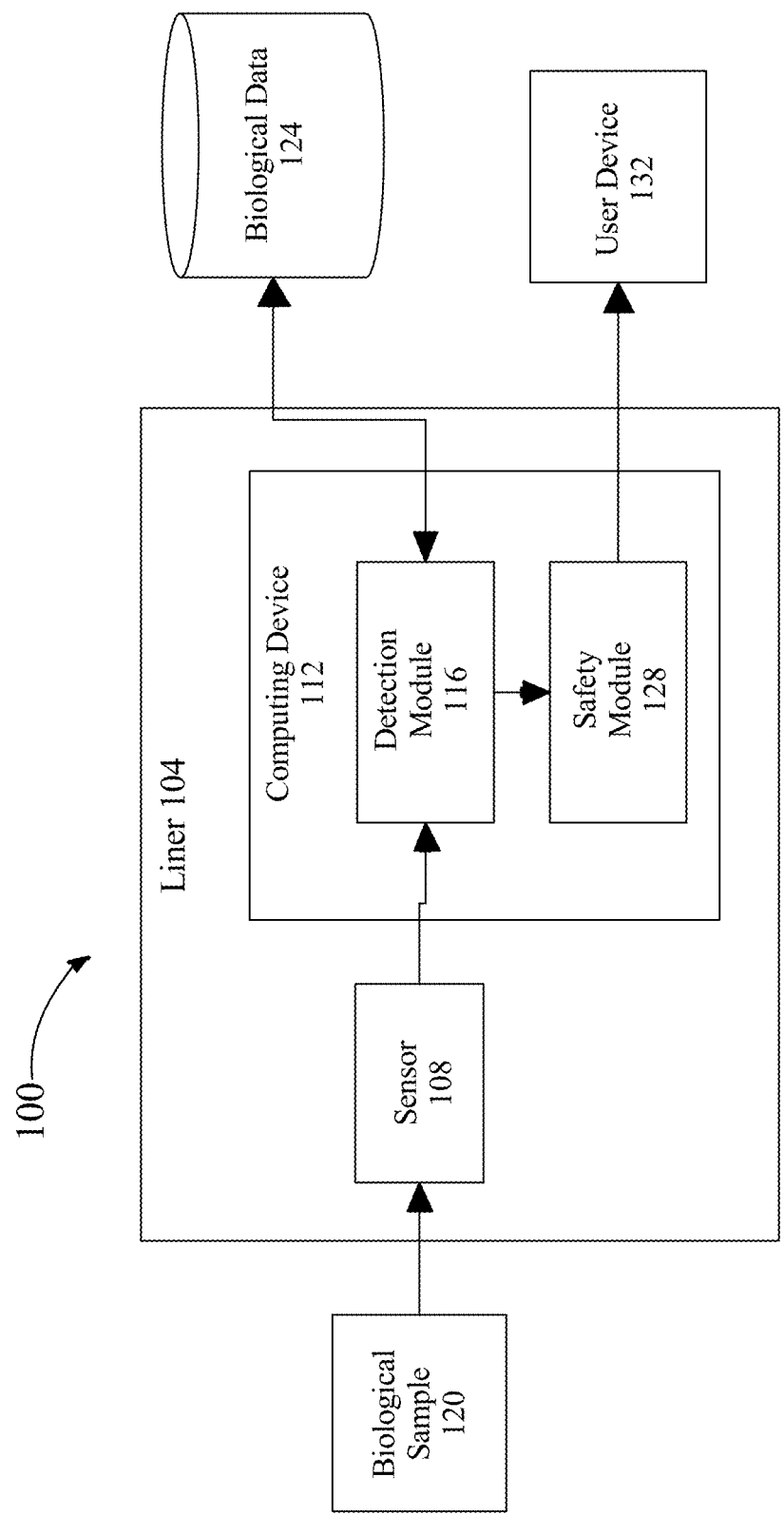
FIG. 1 is a block diagram illustrating an exemplary embodiment of a garment embedded secretion analysis system.

Referring now to FIG. 1, an exemplary embodiment of a apparatus 100 for secretion analysis embedded in a garment is illustrated. Apparatus 100 includes a liner 104. A "liner," as used throughout this disclosure, is an extra piece of fabric that lines a garment with the purpose of absorbing bodily fluids. As used herein, "bodily fluids" are liquids held that may be expelled and/or excreted from a human body. Bodily fluids may include, without limitation, sweat, urine, mucus, blood, menstrual blood, saliva, fecal matter, semen, or vaginal fluids such as discharge. Moreover, liner 104 may comprise an absorbent material to capture these bodily fluids. Absorbent materials used may be, but without limitation, cellulose, natural fibers, microfibers, absorbent gel material, or any other material configured to absorb fluid. In some embodiments, liner 104 may also be made of non-absorbent material. In some embodiments, liner 104 may be configured to change color based o the presence of certain biomarkers, such as increased salt level, presence of protein in urine (proteinuria), or/and hormones, such as a human chorionic gonadotropin (hCG). In a nonlimiting example, liner 104 may be configured to change to a blue color when droplets of urine that come in contact with liner 104 contains high levels of a pregnancy related hormone, such as the hCG hormone.

Continuing to refer to FIG. 1, liner 104 includes at least a sensor 108 from a plurality of sensors. As used herein, a "sensor" is a device, module, and/or subsystem, utilizing any hardware, software, and/or any combination thereof to detect events and/or changes in the instant environment and transmit the information; transmission may include transmission of any wired or wireless electronic signal. At least a sensor 108 may include any electromagnetic sensor, including without limitation electroencephalographic sensors, magnetoencephalographic sensors, electrocardiographic sensors, electromyographic sensors, or the like. At least a sensor 108 may include a temperature sensor. At least a sensor 108 may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a sensor 108 may detect heart rate or the like. At least a sensor 108 may detect any hematological parameter including blood oxygen level, pulse rate, heart rate, pulse rhythm, blood sugar, and/or blood pressure. At least a sensor 108 may be configured to detect internal and/or external biomarkers and/or readings. At least a sensor 108 may be a part of system 100 or may be a separate device in communication with apparatus 100. Sensor or at least a sensor 108 are used interchangeably throughout this disclosure. At least a sensor 108 may include a volatile organic compound (VOC) sensor, such as a chemical and/or an electrochemical sensor. In a nonlimiting example, VOC sensor may detect increased levels of ketone in a user's biological sample, where the increased levels of ketone may mean that the user is undergoing some form of physiological stress. In another non-limiting example, sensor 108 may detect that user is undergoing some physiological stress, such as being robbed at gunpoint, by detecting a spike in user's heart rate while detecting that the user is not performing any movement that would correlate to the elevated heart rate. VOC sensor may include, without limitations, the SD-MSS-1K2GP sensor, made by NanoWorld AG, located at rue des Saars 102000 Neuchatel, Switzerland.

With continued reference to FIG. 1, at least a sensor 108 may be configured to measure body temperature. In this disclosure, "body temperature" is the measure of the internal hotness or coldness of the body of the user. Temperature, for the purposes of this disclosure, and as would be appreciated by someone of ordinary skill in the art, is a measure of the heat energy of a system, or in this case, the body of the user. Temperature, as measured by any number or combinations of sensors present within sensor suite, may be measured in Fahrenheit (° F.), Celsius (° C.), Kelvin (° K), or another scale alone or in combination. The temperature measured by sensors may comprise electrical signals which are transmitted to their appropriate destination wireless or through a wired connection. Additionally, at least a sensor 108 is further configured to measure a property of a bodily fluid. As used herein, a "property" of a bodily fluid refers to a quality or trait of a bodily fluid, especially one that's peculiar or out of place compared to normal. A property of bodily fluids may include any sort of measurement, density, viscosity, surface tension, volume, weight, presence of other fluids, or anything similar. For example, a property of a bodily fluid may include measuring a fertile period by measuring the beginning and end of menstrual blood. Another example of a property of a bodily fluid, without limitation, is the concentrations of components in sweat. Components may include but not limited to urea, uric acid, ammonia, lactic acid, or vitamin C. Another property of a bodily fluid may include viscosity of sweat or even the volume of sweat. Additionally, another property may include, without limitation, the presence of blood in urine. At least a sensor 108 in the plurality of sensors may be configured to include an agent that may change color as a function of the acidity, or the pH, of the urine or another bodily fluid. As used herein, an "agent" is a chemical substance that interacts with a bodily fluid to make a reaction. For example, if urine is above a certain pH, it may appear blue or another color on liner 104. Another example of an agent used may be, without limitation, that if sweat is absorbed by liner 104 an agent emits a scent to cover up the potential stench the sweat may cause.

Still referring to FIG. 1, garment embedded secretion analysis apparatus 100 may be wearable. In some embodiments, Garment embedded secretion analysis apparatus 100 may include a wearable technology. For the purposes of this disclosure, a "wearable technology" is a technological device, such as a computing device and/or processor, which is designed to be worn by a user. For example, wearable technology may include a smart watch. A smartwatch may include, as a non-limiting example, an IWATCH. In some embodiments, wearable technology may include a GPS tracker, a GPS key fob, a fitness tracker, and the like. As a non-limiting example, a fitness tracker may include a FITBIT. In an embodiment, liner may provide geolocation data about a user and may be configured to provide tracking data. In an embodiment, geolocation data may be shared with a third party such as a family member and/or friend who may be concerned about a user's location.

Continuing to refer to FIG. 1, garment embedded secretion analysis apparatus 100 includes a computing device 112 embedded in the liner 104 and communicatively connected to at least a sensor 108. Computing device 112 may be located inside, next to, be embedded in, or any other way to be communicatively connected to at least a sensor 108 in order to detect data. Computing device 112 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 112 may include a single computing device operating independently, or may include two or more computing device operating in concert, in parallel, sequentially or the like; two or more computing devices may be included together in a single computing device or in two or more computing devices. Computing device 112 may interface or communicate with one or more additional devices as described below in further detail via a network interface device. Network interface device may be utilized for connecting computing device 112 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 112 may include but is not limited to, for example, a computing device or cluster of computing devices in a first location and a second computing device or cluster of computing devices in a second location. Computing device 112 may include one or more computing devices dedicated to data storage, security, distribution of traffic for load balancing, and the like. Computing device 112 may distribute one or more computing tasks as described below across a plurality of computing devices of computing device, which may operate in parallel, in series, redundantly, or in any other manner used for distribution of tasks or memory between computing devices. Computing device 112 may be implemented using a "shared nothing" architecture in which data is cached at the worker, in an embodiment, this may enable scalability of apparatus 100 and/or computing device.

With continued reference to FIG. 1, as used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Continuing to refer to FIG. 1, at least a sensor 108 may be attached, mechanically connected, and/or communicatively connected, as described above, to computing device 112. For example, and without limitation, at least a sensor 108 may include any type of sensor needed to detect the data as described herein. For example, at least a sensor 108 may include a temperature sensor, a fluid sensor, and/or the like. At least a sensor 108 may include one or more temperature sensors, which may function to sense temperature of bodily fluids or the internal temperature of the user's body. A temperature sensor may include without limitation one or more sensors used to detect ambient temperature or barometric pressure. Additionally, or alternatively, plurality of sensors may include a geospatial sensor. Plurality of sensors may be located inside liner 104; and/or be included in and/or attached to at least a portion of liner 104. Plurality of sensors may be used to monitor the status of bodily fluids of the user. At least a sensor 104 may be incorporated into garment embedded secretion analysis apparatus 100 or be remote. Plurality of sensors may be communicatively connected to an energy source and/or motor. Plurality of sensors may comprise an electrocardiogram (ECG). As used herein and throughout, an "ECG" is a recording of the heart's electrical activity. At least a sensor 108 may be configured to detect the user's heartbeat through liner 104.

Still referring to FIG. 1, in some embodiments, at least a sensor 108 include be a strain gauge sensor. A "strain gauge sensor," as described herein, is a sensor configured to measure electrical resistance based on changes in strain, where a positive strain is the result of stretching a material and negative strain is the result of compression. In an embodiment, strain gauge sensor is attached to the liner using a silicone film. In some embodiments, sating gauge sensor is a knitted strain sensor. A "knitted strain sensor," as used herein, refers to the strain sensor that is attached to flexible electrically conductive material knitted with the fabric of the liner, where the strain gauge sensor is configured to detect bending deformation of the flexible electrically conductive material through the change of electrical signals in the flexible electrically conductive material. In a nonlimiting example, flexible electrically conductive material may include a silver coated yarn thread.

With continued reference to FIG. 1, computing device 112 may be designed and/or configured to perform any method, method step, or sequence of method steps in any embodiment described in this disclosure, in any order and with any degree of repetition. For instance, computing device 112 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 112 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Referring still to FIG. 1, computing device 112 may be communicatively connected to a database. Database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure. Database may be a biological sample database. One or more tables contained within a biological sample database may include a sensor data table. Sensor data table may include one or more biological date markers obtained from at least a sensor 108. For instance, and without limitation, sensor data table may include menstrual cycle history of a user recorded by at least a sensor 108.

Continuing to refer to FIG. 1, in some embodiments, computing device 112 may be configured to generate a 3D pelvic measurement using the at least a sensor 108, such as the strain gauge sensor described further above. In some embodiments, computing device 112 may be further configured to measure a user's girth, such as user's belly girth. In a nonlimiting example, computing device 112 may generate a 3D pelvic model by generating a three-dimensional graphical representation of the deformations in a flexible electrically conductive material attached to the strain gauge sensor. Persons skilled in art, upon reviewing this disclosure, will recognize the many methods that can be used to generate the 3D pelvic, and/or girth measurements, using the at least a sensor 108.

Still referring to FIG. 1, computing device 112 includes a detection module 116 configured to extract at least a biological sample from the user. Detection module 116 may be part of computing device 112. In an embodiment, detection module 116 may be a separate computing device communicatively connected to computing device 112. In a further embodiment, detection module 116 may be a separate computing device communicatively connected to at least a sensor 108. In an embodiment, extraction of biological includes biological samples passively gathered by at least a sensor 108, such as through touching the user's skin, touching particles of sweat, particles of urine and the like. "At least a biological sample," as used in this disclosure, includes any sample obtained from a human body of a user. At least a biological sample 120 may be obtained from a bodily fluid and/or tissue such as sweat, blood, skin tissue, stool sample, hair, urine, and the like. At least a biological sample 120 may be obtained by detection module 116 from at least a sensor 108 in contact with a human body of the user, such as sensor 108 contact with user's skin, sweat absorbed by liner 104 from the user and the like. In a nonlimiting example, in a moment of stress the user may sweat at an elevated rate, the liner 104 may absorb that sweat and detection module 116 may detect the biological sample from user through sensor 108 embedded in the liner 104. In another nonlimiting example, biological sample may be a vaginal discharge, which detection module 116 may extract by absorbing the sample through liner 104. In a nonlimiting example, detection module 116 may extract a user skin tissue sample through sensor 108 direct contact with user's skin. In some embodiments, detection module 116 may be configured to use a spectroscopic method. In an embodiment, detection module 116 may be configured to use a colorimetric method. In some embodiments, and without limitation, detection module 116 may be configured to use any detection method. Persons skilled in the art, upon reviewing this disclosure, will recognize the plurality of detection methodologies that detection module 116 may be configured to use.

Still referring to FIG. 1, another property of a bodily fluid that detection module 116 detects may include indication of a presence of a date rape drug in the bodily fluid. As used in this disclosure, a "date rape drug" refers to a drug, usually given involuntarily to the user, drug that causes temporary loss of memory or inhibition, surreptitiously given to someone in order to facilitate rape or sexual abuse. Types of date rape drugs include, but without limitation, gamma-hydroxybutyric acid (GHB), flunitrazepam also known as Rohypnol, ketamine, alcohol, marijuana, or any drug that inhibits a person. Though these drugs are not exclusively used for such purposes but are the properties or side-effects of substances normally used for legitimate medical purposes. Sensors in detection device 112 may be configured to detect the presence of a date rape drug in any bodily fluid that interacts with liner 108. Plurality of sensors may be configured to specifically detect flunitrazepam. Furthermore, detection device 112 may transmit an alert to any device described herein of the presence of such drugs in the body of the user or may use an agent to show its presence as described above.

Still referring to FIG. 1, detection module 116 is configured to authenticate the user as a function of the biological sample 120 and biological data 124 of the user. In an embodiment, authentication may be a biometric authentication. A "biometric authentication," as used herein, is a characteristic of the user that verifies the user's identity. Detection module 116 may not be able to perform any of the step as described herein until it receives biometric authentication. Biometric authentication may be detected by detection module 116 or may be inputted by a user into any of the devices described herein. Biometric authentication may include, for example, scanning a user fingerprint, scanning an iris, taking a blood sample, pH level, and/or measuring the gait of a user. Biometric authentication may ensure that any of the devices described herein are being used by the owner of user device, the user. In an embodiment, biometric authentication may be unimodal whereby only one biometric authentication is performed, or biometric authentication may be multimodal whereby two or more biometric authentications are performed. For example, a multimodal authentication may include a fingerprint scan and a blood sample. In an embodiment, multimodal authentication may be simultaneous, whereby two or more biometric authentications are occurring at the same time, or multimodal authentication may be performed in succession, whereby one biometric authentication is performed followed in succession by at least a second biometric authentication. In an embodiment, biological data 124 is store in a biological sample database related to the user. Biological sample database is described in further detail in FIG. 3 further below. Detection module 116 may compare biological sample 120 of user to biological data 124 to identify the user that the biological sample 120 belongs to. In some embodiments, detection module 116 may only detect a condition datum if the user that biological sample 120 belongs to is authorized to use the garment embedded secretion analysis apparatus 100. In an embodiment, a plurality of users may be associated and authorized to use garment embedded secretion analysis apparatus 100. Detection module 116 may be configured to update biological data 124. In a nonlimiting example, detection module 116 may update the user's biological data 124 with the biological sample 120 extracted from the user.

Continuing to refer to FIG. 1, computing device 112 may further include an activation device. As used herein, an "activation device" is a device configured to initiate a reaction to something. In an embodiment, an activation device on garment embedded secretion analysis apparatus 100 may activate the detection module 116. Activation device may also initiate safety module 128 to contact the user or another device or organization. In an embodiment, safety module 128 may generate an alert datum as a function of the activation device. Moreover, activation device may be any sort of device that initiate and ceases actions, such as an on/off switch, a button, a joystick, a pressure switch, a temperature switch, or the like. Activation device may be located on the waistband of the underwear garment, or anywhere else that can be easily accessible to the user. In a nonlimiting example, safety module 128 may generate an alert datum and transmit the alert to emergency services based on the user activating the activation device, such as pressing a button on the device.

With continued reference to FIG. 1, detection module 116 is configured to detect a condition datum as a function of the at least a biological sample 120 and biological data 124. In a nonlimiting example, detection module 116 may detect condition datum by comparing the at least a biological sample 120 of the user to the biological data 124 of the user, such as comparing presence of blood in urine particles to biological data of the user that includes information related to user's ongoing kidney condition, in which case detection module 116 would detect that blood in urine is a condition related to user's kidney condition. Detection module 116 may detect an event that indicates a threat to a user and transmit it to safety module 128. As used in this disclosure, "condition datum" describes a condition associated with the biological sample 120 from the user. In a nonlimiting example, event datum may include a description signaling that an unknown chemical was detected in user's biological sample 120. In another nonlimiting example, condition datum may include the detection of blood in the biological sample 120. In another example, without limitations, condition datum may include a spike in user's body temperature. Detection module 116 may be configured to detect a condition datum as a function a user data. In another nonlimiting example, biological sample 120 may include blood in urine of a user going through her menstrual cycle, in this case detection module 116 may not detect a condition datum after comparing biological sample 120 to biological data 124 of the user since the presence of blood in urine at the level present in the sample would be within an expected threshold.

Continuing to refer to FIG. 1, user data may include one or more evaluations of sensory ability, including measures of audition, vision, olfaction, gustation, vestibular function and pain. User data may include genomic data. User data may include data concerning a microbiome of a person, which, as used herein, includes any data describing any microorganism and/or combination of microorganisms living on or within a person, including without limitation biomarkers, genomic data, proteomic data, and/or any other metabolic or biochemical data useful for analysis of the effect of such microorganisms on other user data of a person, and/or on at least a prognosis and/or ameliorative processes.

With continued reference to FIG. 1, user data may further include information concerning the user's fertility and flow of their menstrual cycle. As used herein, "fertility" refers to capability to produce offspring through reproduction following the onset of sexual maturity, while "flow" is the intensity of blood loss while the user experiences a menstrual cycle. User data may include any information about the user's fertility and flow history, when the user is most likely to be able to get pregnant, if the user is pregnant, the user's fertility window, the user's next predicted menstrual cycle, what day of their menstrual cycle the user is on, if the user's menstrual cycle has bled through the garment, density of the user's menstrual blood, which phase of their menstrual cycle the user is experiencing, and any other information relevant to the user's fertility or uterine health. In an embodiment, user data may include information relating to a user's diet. This may include, without limitation, any data concerning what the user eats, if the user has any food allergies or sensitivities, the user's body mass index, which nutrients the user is lacking, or any other data concerning what the user has consumed. Also, user data may include information relating to a user's mental health. This may include any data that may be detected relating to the mental health history or current mental health state of the user. In a nonlimiting example, detection module 116 may determine a condition datum of an unexpected presence of blood outside a user's menstrual cycle. In another nonlimiting example, detection module 116 may detect a condition datum of a prolonged elevated level of sweating in a user that has diabetes.

Referring still to FIG. 1, computing device 112 may include a data inference engine configured to process data from detection module 116. In an embodiment, detection module 116 may be configured to determine event datum as a function of the data inference engine. As used herein, a "data inference engine" is a database engine software component that makes a decision from the data contained in the database of apparatus 100 or the algorithm derived from a deep learning AI system. Data inference engine may be transmitted data detected from at least a sensor 108. Data may be any of the data described above or herein. Data inference engine takes this data from detection module 116 and deduces new information. Such new information may consist of, without limitation, deducing the user's next menstrual cycle, determining if the user's body temperature is medically concerning, sending an alert to another device, deciding that the blood alcohol content of the user is concerningly high, to anything that a device may need to infer using data received. Data inference engine may work primarily using forward chaining or backward chaining. "Forward chaining" is a mode that starts with the available data and uses inference rules to extract more data until a goal is reached, while "backward chaining" is another mode that works backward from the goal. Data inference engine may be cloud-based. As used herein, "cloud-based" may refer to stored, managed, and processed on a network of remote servers hosted on the internet, rather than on local servers or personal computers. Data inference engine may also use local servers or personal computers. Data inference engine may also be available via a WIFI network. Data inference engine may use a machine-learning model, neural network, classifier, or any other AI architecture as described herein. In an embodiment, data inference engine may be configured to receive and/or analyze data from one or more wearable devices to improve any health, wellness, and/or safety index. A "wearable device" as used in this disclosure, is any electronic device that may be worn by a user as an accessory, embedded into clothing, implanted into a user's body, and/or tattooed onto a user's skin. In an embodiment, detection module 116 may determine a condition datum as a function of data inference engine. Data inference engine may include a machine-learning model trained to correlate a measurement from detection module 116 to a user. The data may include, but not limited to how fertile the user is at the time of the measurement, a current or potential disease state of a user, the level of libido, a user's body chemistry level, or the like. Data inference engine may perform determinations, classification, and/or analysis steps, methods, processes, or the like as described in this disclosure using machine learning processes. A "machine learning process," as used in this disclosure, is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language. Data inference engine may be designed and configured to create a machine learning model consistent with any machine-learning model described herein. Training data and machine learning models/algorithms are described in more detail further below in FIGS. 4-7.

Still referring to FIG. 1, detection module 116 is configured to determine an event datum as a function of the condition datum. An "event datum," as used herein, is a description of an event that may impact the user's safety and/or health. In a nonlimiting example, detection module 116 may detect the presence of the chemical associated with rape drugs in biological sample 120, such as gamma-hydroxybutyric acid (GHB), and may determine that the user has been drugged as an event datum. In another nonlimiting example, detection module 116 may determine that the diabetic user is hypoglycemic based on a condition datum of prolonged elevated sweating. In another nonlimiting example, detection module 116 may detect blood in urine of a user with an ongoing kidney disease, and may determine an event datum that describes the blood in urine as a possible kidney infection. In an embodiment, event datum may be determined as a function of a machine learning model. Machine learning model may receive elements in a biological sample as inputs and output at least an event datum. In embodiments, machine-learning model may utilize training data, where training data may include correlations of sample data for elements in a biological sample to at least an event datum. In a nonlimiting example, training data may include a correlation of heart rates with user movements to a possible event datum. Such as, and without limitation, a level of increase in heart rate and a measured amount of user movement may be correlated to possible physiologically stressful situations, where a high level of increase in heart rate while only a minimum level of user movement is detected may mean that the user is undergoing a stressful event. Training data may include sample data. Training data may include data inputted by the user. Training data may include past correlations of machine-learning model. Machine learning model may be trained by computing device 112 and/or a remote device. Training data and machine learning models/algorithms are described in more detail further below in FIGS. 4-7.

With continued reference to FIG. 1, in a nonlimiting example, detection module 116, using a machine-learning model, may be configured to correlate the detection of blood in biological sample 120 with a user's menstrual cycle and generate an event datum if blood is detected when user is not on her period. Machine-learning model may be trained, without limitations, using training data correlating blood biological samples 120 for a plurality of users with a plurality of stages of a menstrual cycle, where outputs may be determined based the quantity of blood detected, the age of the user, hygiene methods, and the like. Training data and machine learning model may be consistent with, or include, any training data and/or machine learning model/algorithm described throughout this disclosure.

With continued reference to FIG. 1, in another nonlimiting example, detection module 116, using a machine-learning model, may be configured to correlate chemical elements detected in biological sample 120 to possible incapacitating intoxication, and generate an event datum if chemical is determined to possibly incapacitate the user, such as rape drugs. Machine-learning model may be trained, without limitations, using training data correlating chemical elements, quantities of the element, medical uses of chemical, such as prescription drugs, to incapacitating scenarios, where outputs may be determined based on quantity of element that may cause incapacitation, whether detection is a discharge from prior medical use, possible natural occurrence of the detected element in the body, sample scenarios of incapacitating use of the element, and the like. Training data and machine learning model may be consistent with, or include, any training data and/or machine learning model/algorithm described throughout this disclosure.

Continuing to refer to FIG. 1, computing device 112 includes a safety module 128 configured to receive event datum. Safety module 128 may be part of computing device 112. In an embodiment, safety module 128 may be a separate computing device consistent with any computing devices described herein. In some embodiments, safety module 128 may be a separate computing device communicatively connected to computing device 112. As described herein, a "safety module" is a piece of technology that helps eliminate or notify user, or others, of a threat to the user.

Still referring to FIG. 1, safety module 128 is configured to generate an alert datum as a function of the event datum. An "alert datum," as used in this disclosure, is data, or an element of data, that describes, or signals, a possible threatening or harmful situation. In an embodiment, alert datum may be generated in textual form. In an embodiment, alert datum may include an alert category. An "alert category," as used herein, is a level of emergency related to the alert datum, which may include, without limitations, a non-emergency category, a possible emergency category, an immediate emergency category, and the like. In a nonlimiting example, alert datum may have a non-emergency category, such as an alert recommending that the user see a gynecologist based on the presence of yeast infection on biological sample 120. In another nonlimiting example, alert datum may be an emergency category, such as if the user is unconscious and an alert is sent out to multiple user devices alerting of the emergency. In some embodiments, alert datum may be an audio signal. In embodiments, alert datum may be a visual representation configured to be displayed through a GUI. In some embodiments, alert datum may be vibration signal. In a nonlimiting example, and following the example above, after detection module 116 determines that user may have possibly been drugged, safety module 128 may generate an alert datum describing the presence of a rape drug in the user's system. In another nonlimiting example, alert datum may be a sound alert, where a computing device may emit a high pitch sound when alert datum describes a possible emergency, such as the user becoming unconscious. In some embodiments, safety module 128 may notify or alert emergency services of a threat. In other nonlimiting examples, alert datum may include a textual alert notifying a diabetic user of low glucose levels detected and an accompanying vibration signal as to grab user's attention to the textual description of the alert datum. In a further example, without limitations, when detection module 116 continues to detect lowering levels of glucose after first alert datum is generated, safety module 128 may generate an audio signal alerting the user, and possibly other people near the user, of the possibly dangerous lower levels of glucose detected. A "threat" to a user is anything that may cause damage or danger to the user. Safety module 128 may be configured to notify the user of the presence of a threat. A threat to the user may include, without limitation, a gender-based violence, a concerning level of drugs or alcohol in the user's system, losing too much blood, or anything else that may endanger the user. Safety module 128 may be enabled by the user in case of a threat to the user, wherein safety module 128 may only contact others as a result of a user input granting safety module 128 permission to be enabled.

Still referring to FIG. 1, in a nonlimiting example, safety module 128, using a machine-learning model, may be configured to correlate presence of a chemical associated with rape drugs to a possible immediate incapacitation, where safety module 128 may generate an emergency category alert datum. Machine-learning model may be trained, without limitations, using training data correlating chemical elements to effects in a user's body, where output may be determined based on type of chemical element detected, extent of effect in a user's body, amount of time chemical detected takes to incapacitate user, and the like.

With continued reference to FIG. 1, in another nonlimiting example, safety module 128, using a machine-learning model, may be configured to correlate a detected yeast infection with possible complications related to the presence of the fungus in biological sample 120, where safety module 128 may generate a non-emergency category, such as an alert advising user to take an antifungal medication, or an emergency category alert datum, such as advising user to seek immediate help or sending an alert to user's gynecologist, based on correlation. Machine-learning model may be trained, without limitations, using training data correlating amounts of fungus detected with number of times fungus have been continuously detected, where outputs may be determined based on sample quantities of fungus detection, rate of increase of fungus culture detected over a period of time, hygiene methods used by users, and the like.

Still referring to FIG. 1, in an example, without limitations, safety module 128, using a machine-learning model, may be configured to correlate a spike in heart rate and user's movements with GPS location of the user, where safety module 128 may generate an alert datum, without limitations, with a "possible emergency" category, such as informing another user of user's location, an "immediate emergency" category, such as sending user's location and a description of the emergency to emergency services, or a non-emergency category, such as advising user to avoid staying in the detected location due to safety risks. Machine-learning model may be trained, without limitations, using training data correlating levels of heart rate increase and levels of user movements to locations marked as unsafe or possibly unsafe depending on time of day, where outputs may be determined based on sample user fitness levels, possible situations justifying a spike in heart rate without correlated user movements, location, times of day where location is considered unsafe, past outputs near detected location for other users, and the like.

Continuing to refer to FIG. 1, in an embodiment, safety module 128 may be configured to determine alert datum as a function of the event datum and the data inference engine. Data inference engine may include a machine-learning model trained to correlate event datum to an alert datum. In an embodiment, machine-learning model may utilize training data correlation sample event datum outputs, or previous outputs for the user, to sample data that includes situations or harmful events that may correlate to the event data. In a nonlimiting example, training data may include an event datum describing the detection of fungus is a vaginal discharge biological sample correlated to a possible vaginal yeast infection. In another nonlimiting example, training data may include event datum describing a possible physiologically stressful situation, such as when sudden spike in heart rate is detected while minimum user movement is detected, correlated to high crime areas. In this example, without limitations, safety module 128 may generate an alert datum describing a possible threat to the user, such as a robbery. Training data may include sample data. Training data may include data inputted by the user. Training data may include past correlations of machine-learning model. Machine learning model may be trained by computing device 112 and/or a remote device. Training data and machine learning models/algorithms are described in more detail further below in FIGS. 4-7.

Still referring to FIG. 1, computing device 112 may be configured to generate a course of action output as a function of the alert datum. A "course of action output," as described herein, is a set of instruction that the user may follow based on the alert datum generated. In an embodiment, course of action may be transmitted to another user, or a plurality of user. In an embodiment, course of action output may be generated as a function of a machine-learning model. In embodiments, machine learning model may be configured to receive alert datum and other data generated by at least a sensor 108 and output a course of action. In a nonlimiting example, machine learning model may take a an alert datum describing a physiological stress and a GPS location of the user as inputs and may generate an output describing the location of the nearest business, or other populated area, where user can seek help. In an embodiment, course of action output machine learning model may be trained using training data. Training data may include past alert datums generated at a specific area, which may be one or more GPS locations or a geographical area, correlated to past course of action outputs, which may include previous outputs from machine-learning model. In a nonlimiting example, high stress alerts that have been detected in a certain area may be correlated to known populated addresses within that area, such as a list of businesses in that area. In an embodiment, a number of alert datums detected over a period of time may be correlated to a course of action output suggesting that user seek professional help. For example, and without limitations, the generation of multiple alert datums over a period of days for an yeast infection may cause computing device 112 to generate a course of action output suggesting that user seek a gynecologist, such as when fungal growth may be growing at a rate where antifungal medication is not enough and antibiotics may be required. Training data may include sample data. Training data may include data inputted by the user. Training data may include past correlations of machine-learning model. Machine learning model may be trained by computing device 112 and/or a remote device. Training data and machine learning models/algorithms are described in more detail further below in FIGS. 4-7.

With continued reference to FIG. 1, computing device 112 may be configured to use a communication protocol. A "communication protocol," as used herein, is a system of rules that allows to devices to communicate and transmit information. Communication protocol may include, without limitation, rules, synchronization, syntax, and semantics of communication between the devices. Communication protocol may include any of the hardware or software as described herein. Communication protocol may be included in safety device 116 or any other device as described herein. Communication protocol may include near-field communication (NFC) or radio frequency identification (RFID). Communication protocol may include, including without limitation internet protocol (IP), controller area network (CAN) protocols, serial communication protocols (e.g., universal asynchronous receiver-transmitter [UART]), parallel communication protocols (e.g., printer port IEEE 128), and the like.

Still referring to FIG. 1, safety module 128 may be configured to transmit the alert datum of a threat to user device 132. In an embodiment, transmitting an alert datum to user device 132 may include contacting emergency services in case of a threat to a user. As used herein, "emergency services" refer to rescue services that ensure public safety and health, such as the police, fire department, medical services, or any other department that can provide help to the user. In an embodiment, transmitting an alert datum to user device 132 may include notifying family members, or any other person configured by the user. In an embodiment, user device 132 may include a wearable device worn by the user. In an embodiment, alert datum that may be transmitted to user device 132 may be the potential presence of a date rape drug, as described above. In another embodiment, another alert datum transmitted to user device 132 may be an alert notifying the user or others if the user's blood alcohol content is reaching a medically concerning level, meaning that the level of alcohol in their system may affect their health. Additionally, another example of a threat, without limitation, is any sort of abnormality in the health of the user, such as low vitamin levels. In such cases, safety device may notify or alert the user rather than emergency services since the safety of the person is not in jeopardy. In an embodiment, safety module 128 may be configured to send out the location of the user when activated using a global positioning system. In such situation, garment embedded secretion analysis apparatus 100 is used to help prevent assault and protect the user from being a victim. In another embodiment, user device 132 may be a computing device attached to a vehicle. In a further embodiment, computing device attached to a vehicle may be an ignition interlocking device. An "ignition interlocking device," as used herein, is a device connected to a vehicle that prevents the operation of the vehicle when device is activated. In a nonlimiting example, detection module 116 detects the presence of alcohol at a level that is unsafe to operate a vehicle, in such case safety module 128 may transmit an alert to the user's vehicle preventing its operation until detection module 116 detects an alcohol level in user's system that is a threshold for safely operating a vehicle.

Still referring to FIG. 1, computing device 112 may further include a global positioning system. As used in this disclosure, a "global positioning system," also known as GPS, is a satellite-based navigation system composing of satellites, ground stations, and receivers. The satellites circulate Earth and constantly are sending out signals, so that the ground stations may use radar to make sure the satellites are located where they should be. The receiver, which in this case is the safety device, wearable device, output device, or any other device described herein, is constantly searching for a signal from these satellites and figures out how far away they are from the satellite; this distance is then used to find the exact location of the receiver. Once the receiver calculates its distance from four or more GPS satellites, it may be configured to figure out where the exact location of the receiver is. GPS may calculate the latitude, longitude, and height position of a user. Furthermore, safety device may include a global positioning system sensor to calculate distance or height. global positioning system sensor may be any of the sensors as described herein.

Continuing to refer to FIG. 1, computing device 112 may also include a reporting engine. In an embodiment, transmitting alter datum to user device 132 may include utilizing reporting engine. As used herein, a "reporting engine" is a database engine software component that is configured to receive data and report it to a specific device, person, organization, or the like. In an embodiment, reporting engine may be used to report data to a user, emergency services, or any other device or organization described herein. Reporting engine is configured to report results to a user device 132 from the data inference engine. As used herein, a "user device" is a device configured to display information to someone or something. Interaction of user with a user device 132 may be through an input device. Examples of an input device include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, an inceptor stick, and any combinations thereof. Also, user device 132 may include a wearable smartwatch, an activity tracker, a smartphone, a mobile app. In non-limiting illustrative examples, wearable device data may include without limitation accelerometer data, pedometer data, gyroscope data, electrocardiography (ECG) data, electrooculography (EOG) data, bioimpedance data, blood pressure and heart rate monitoring, oxygenation data, biosensors, fitness trackers, force monitors, and the like, as described above. User device 132 may receive input from user, emergency services, family members, etc. through standard I/O interface such as ISA (Industry Standard Architecture), PCI (Peripheral Component Interconnect) Bus, and the like. Output device may receive input from user through standard I/O operation. In one embodiment, user device 132 may further receive input from user through optical tracking of motion. In one embodiment, user device 132 may further receive input from user through voice-commands. User device 132 may further use event-driven programming, where event listeners are used to detect input from user and trigger actions based on the input.

Continuing to refer to FIG. 1, reporting engine includes a dashboard. A "dashboard" is a graphical user interface facing a user that may contain instruments and/or controls. Dashboard may include user demographic data, the particular measurement from a sensor, the state, contact information for the user's healthcare practitioner, data comparing the user to other users of the same gender, age group, suggestion for improving the user's health (diet and exercise suggestions), suggestions for increasing the user's libido, or suggestions for improving the user' general well-being. Any of the data described herein may be displayed in dashboard.

Figure 2A:
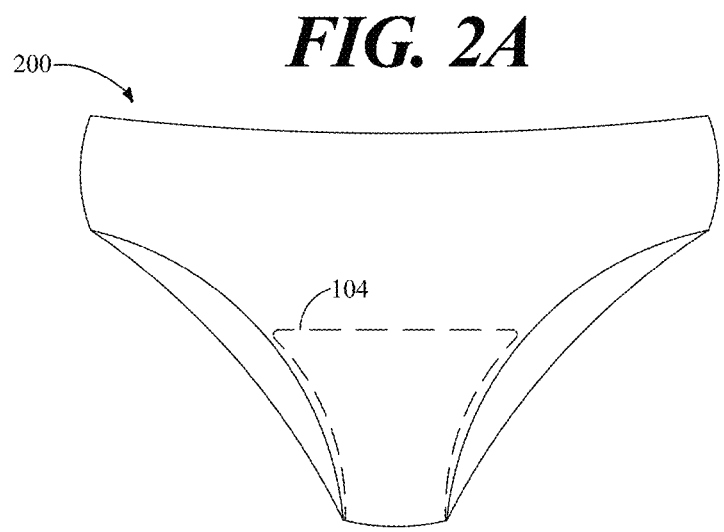
FIG. 2A shows a front view of an exemplary embodiment of a garment embedded secretion analysis system.
Figure 2B:
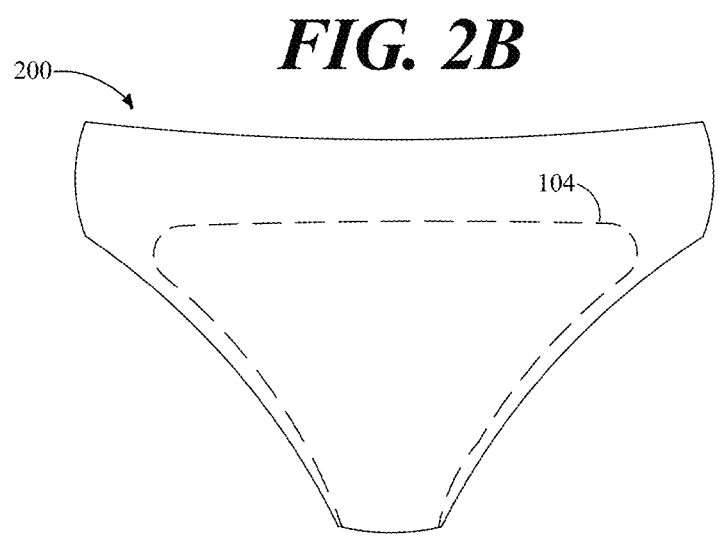
FIG. 2B shows a back view of an exemplary embodiment of a garment embedded secretion analysis system.

Now referring to FIGS. 2A and 2B, a front view and a back view of an exemplary embodiment of a secretion analysis apparatus 100 embedded in an underwear garment is presented. Liner 104 may cover just a portion of the underwear garment as seen in the figure or may be a lined throughout the inside the entire underwear garment. In a nonlimiting example, garment may be an underwear. In another nonlimiting example, garment may be a pair of socks.

Figure 2C:
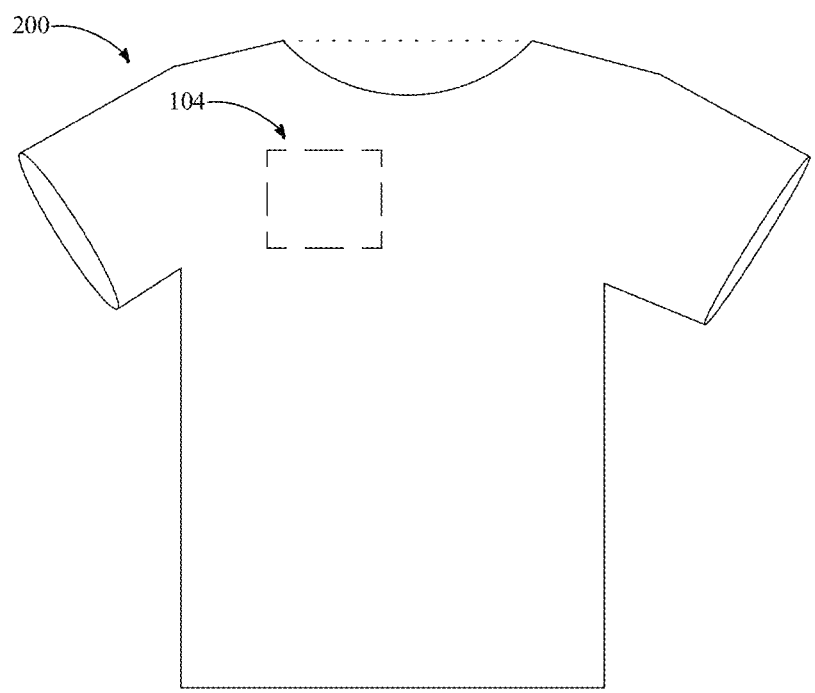
FIG. 2C shows a front side of an illustrative embodiment of a garment embedded secretion analysis system.

Now referring to FIG. 2C, a front view of an exemplary embodiment of a secretion analysis apparatus 100 embedded in a t-shirt garment is illustrated. Liner 104 may be embedded in any portion of the t-shirt garment that is in direct contact with the user. Without limitation, garment embedded secretion analysis apparatus 100 may be embedded in any garment that is configured to be in direct contact with the user. In a nonlimiting example, garment may be a shirt. In another example, and without limitations, garment may be a pair of pants.

Now referring to FIG. 2D, an exemplary embodiment of a liner 104 is shown. Liner 104 may be any size or shape as long as it fits within a garment that secretion analysis apparatus 100 is embedded in and is able to perform all the steps as described herein.

Figure 3:
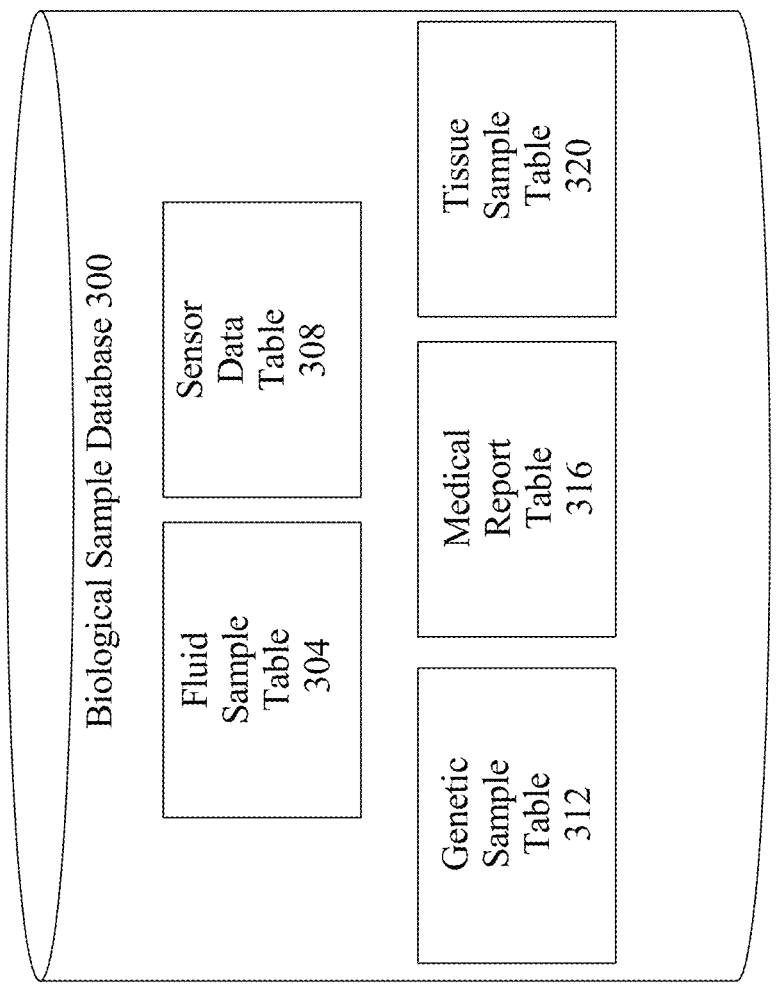
FIG. 3 is an illustrative embodiment of a biological sample database.

Now referring to FIG. 3, an exemplary embodiment of a biological sample database 300 is presented. As a non-limiting example, one or more elements of biological data may be stored in and/or retrieved from a biological sample database 300. "Biological data," includes data related to user data, biological samples associated with the user, and the like. Biological sample database 300 may include any data structure for ordered storage and retrieval of data, which may be implemented as a hardware or software module. A biological sample database 300 may be implemented, without limitation, as a relational database, a key-value retrieval datastore such as a NOSQL database, or any other format or structure for use as a datastore that a person skilled in the art would recognize as suitable upon review of the entirety of this disclosure. A biological sample database 300 may include a plurality of data entries and/or records corresponding to elements of biological data as described above. Data entries and/or records may describe, without limitation, data concerning particular biological samples that have been collected; entries may describe reasons for collection of samples, such as without limitation one or more conditions being tested for. Data entries may include prognostic labels and/or other descriptive entries describing results of evaluation of past biological samples, including diagnoses that were associated with such samples, prognoses and/or conclusions regarding likelihood of future diagnoses that were associated with such samples, and/or other medical or diagnostic conclusions that were derived. Such conclusions may have been generated by apparatus 100 in previous iterations of methods, with or without validation of correctness by medical professionals. Data entries in a biological sample database 300 may be flagged with or linked to one or more additional elements of information, which may be reflected in data entry cells and/or in linked tables such as tables related by one or more indices in a relational database; one or more additional elements of information may include data associating a biological sample and/or a person from whom a biological sample was extracted or received with one or more cohorts, including demographic groupings such as ethnicity, sex, age, income, geographical region, or the like, one or more common diagnoses or physiological attributes shared with other persons having biological samples reflected in other data entries, or the like. Additional elements of information may include one or more categories of biological data as described above. Additional elements of information may include descriptions of particular methods used to obtain biological samples, such as without limitation, capture of data with one or more sensors, and/or any other information concerning provenance and/or history of data acquisition. Persons skilled in the art, upon reviewing the entirety of this disclosure, will be aware of various ways in which data entries in a biological sample database 300 may reflect categories, cohorts, and/or populations of data consistently with this disclosure.

With continued reference to FIG. 3, biological sample database 300 may include tables listing one or more samples according to sample source. For instance, and without limitation, biological sample database 300 may include a fluid sample table 304 listing samples acquired from a person by extraction of fluids, such as without limitation blood, sweat, urine and the like. As another non-limiting example, biological sample database 300 may include a sensor data table 308, which may list samples acquired using one or more sensors, for instance as described in further detail below. As a further non-limiting example, biological sample database 300 may include a genetic sample table 312, which may list partial or entire sequences of genetic material. Genetic material may be extracted and amplified, as a non-limiting example, using polymerase chain reactions (PCR) or the like. As a further example, also non-limiting, biological sample database 300 may include a medical report table 316, which may list textual descriptions of medical tests, including without limitation radiological tests or tests of strength and/or dexterity or the like. Data in medical report table may be sorted and/or categorized using a language processing module 312, for instance, translating a textual description into a numerical value and a label corresponding to a category of physiological data; this may be performed using any language processing algorithm or algorithms as referred to in this disclosure. As another non-limiting example, biological sample database 300 may include a tissue sample table 320, which may record biological samples obtained using tissue samples, such as a user's dead-skin. Tables presented above are presented for exemplary purposes only, persons skilled in the art will be aware of various ways in which data may be organized in biological sample database 300 consistently with this disclosure.

Figure 4:
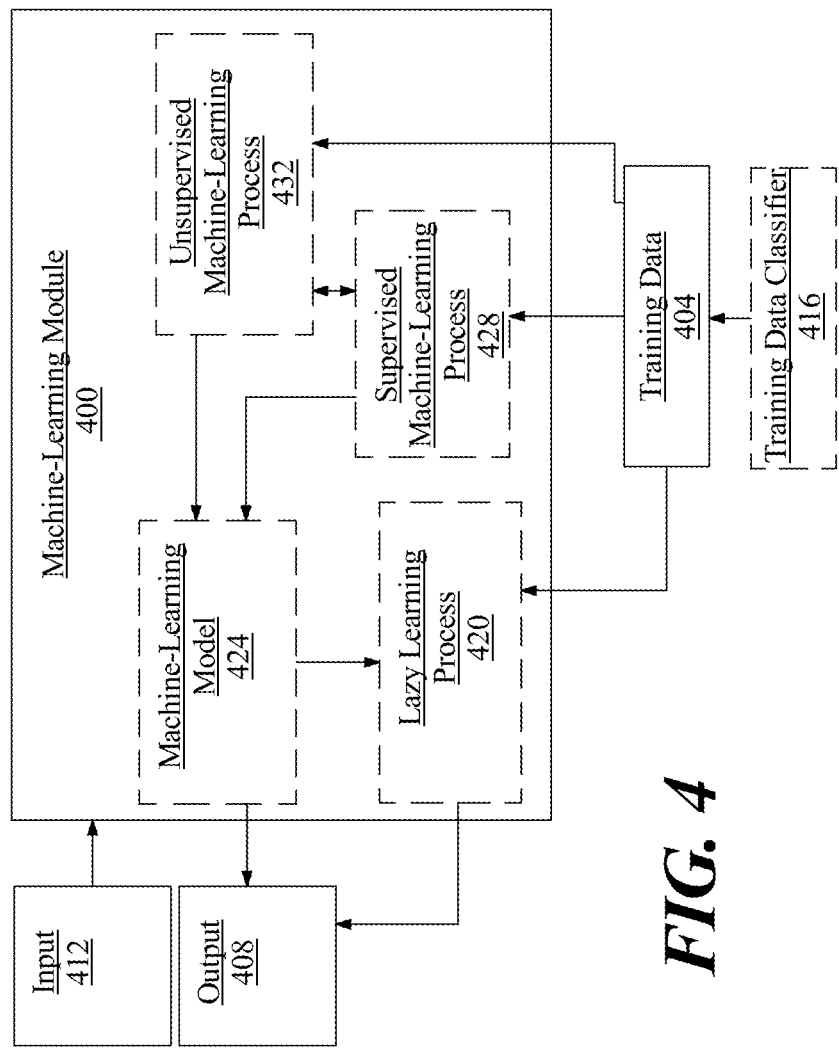
FIG. 4 is a block diagram of an exemplary embodiment of a machine-learning module.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example training data may correlate a presence of blood in a urine sample to an inflammation of the kidneys.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to a possible pregnancy based on a person's sex and menstrual cycle.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include urine samples as described above as inputs, possible urinary diseases as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Figure 5:
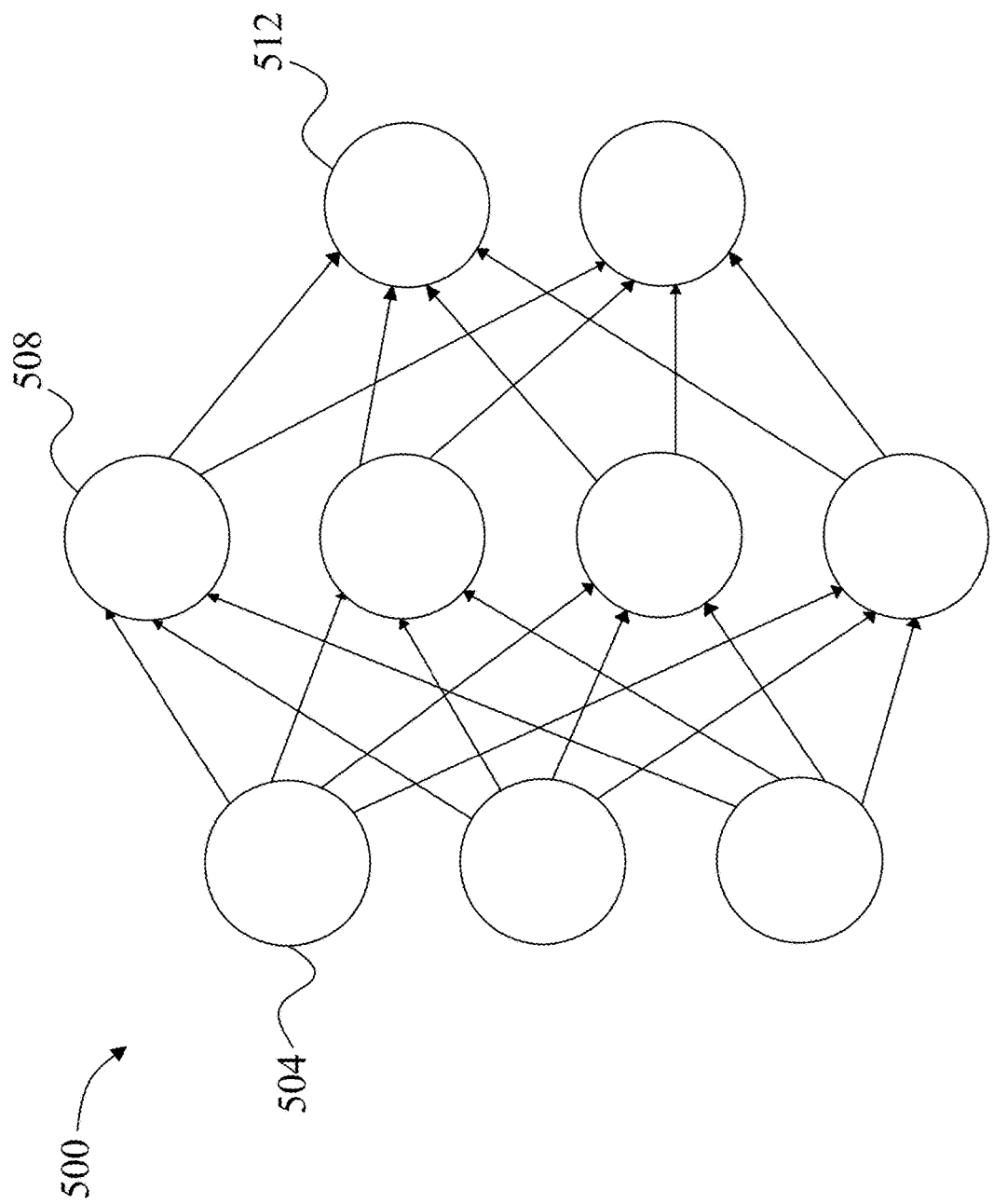
FIG. 5 is a block diagram illustrating an exemplary embodiment of a neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 6:
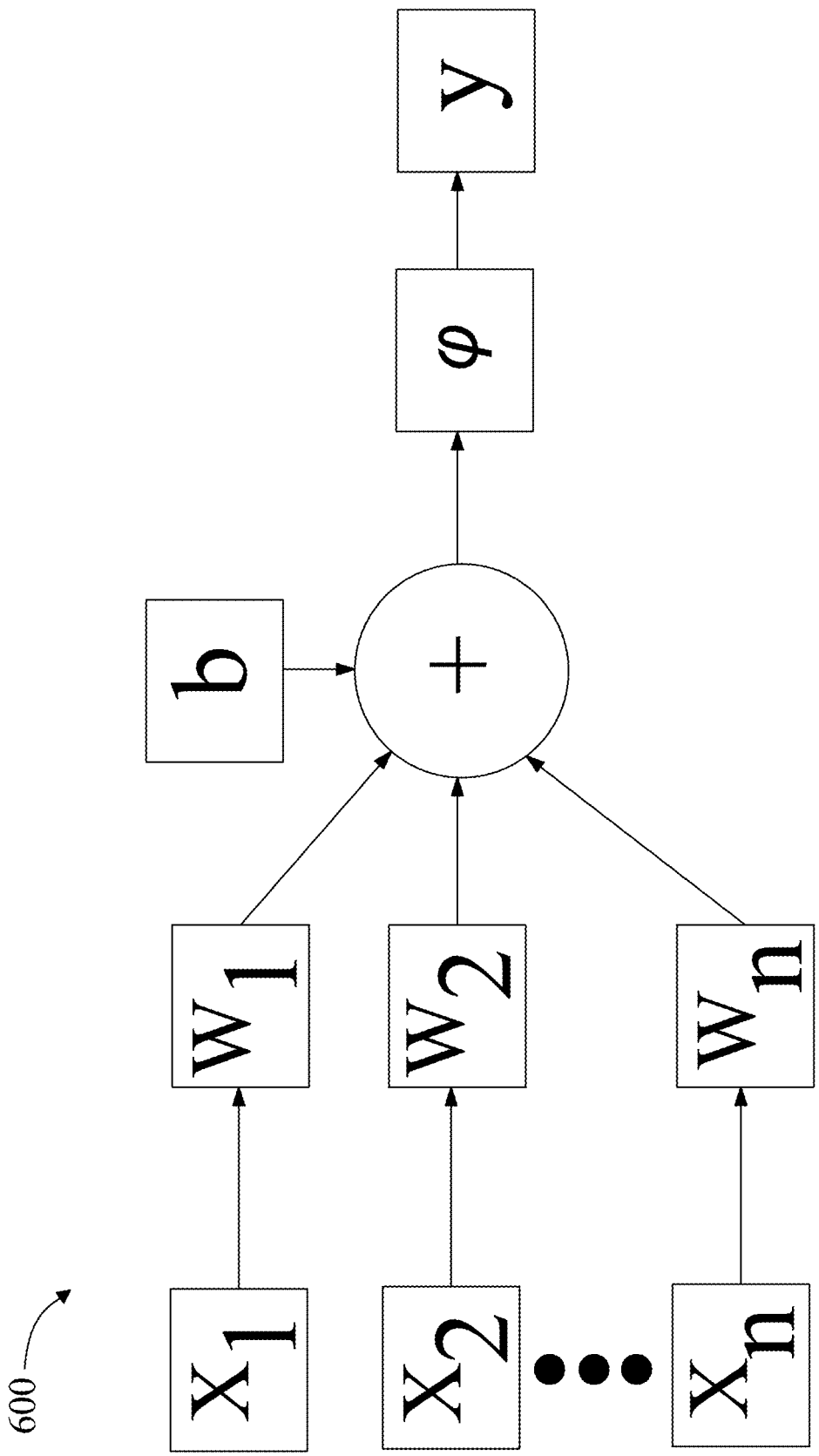
FIG. 6 is a diagram of an exemplary embodiment of a node of a neural network.

Referring now to FIG. 6, an exemplary embodiment of a node of a neural network is illustrated. A node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally, or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 7:
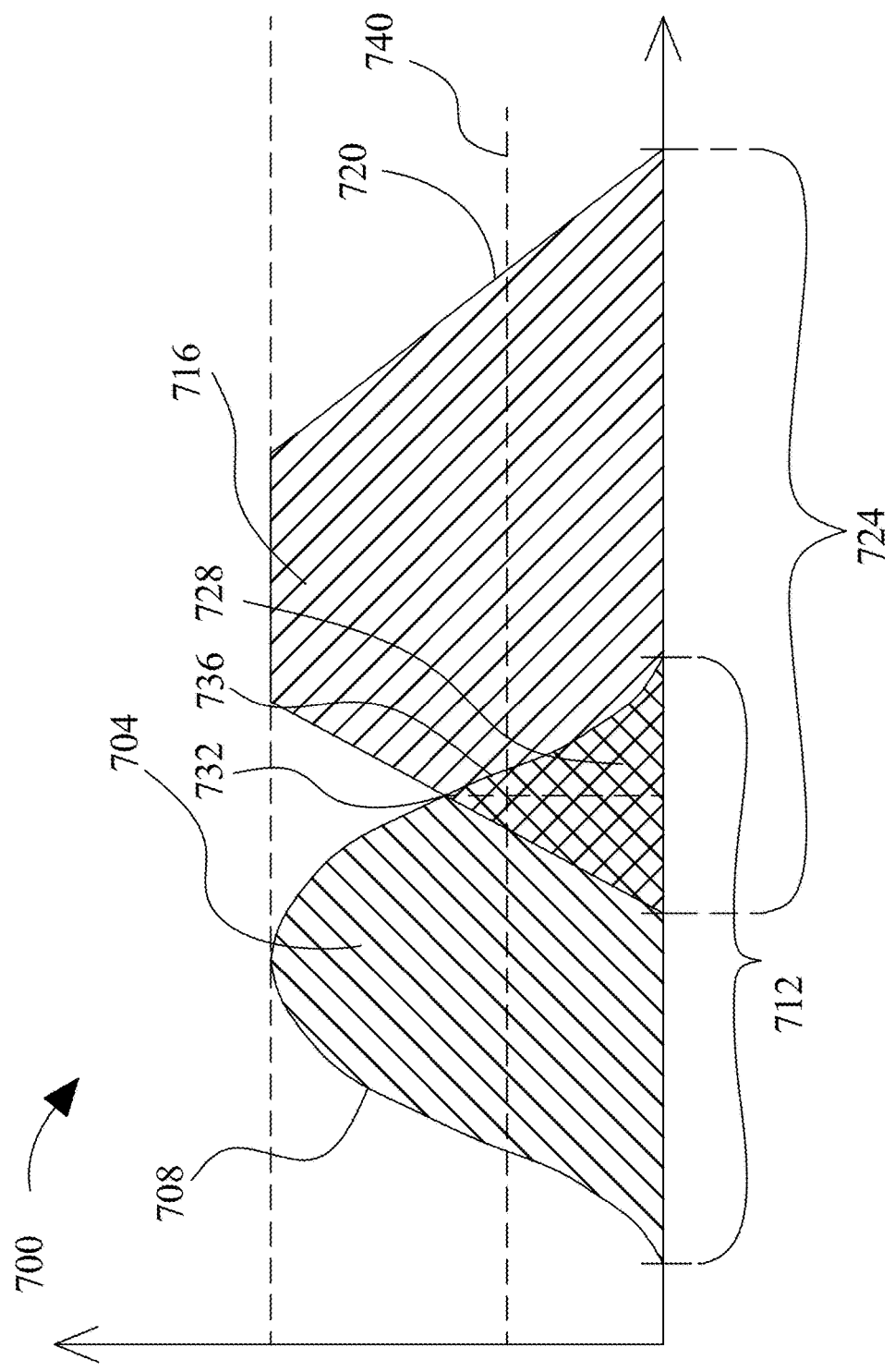
FIG. 7 is a diagram of an exemplary embodiment of a fuzzy set comparison.

Referring to FIG. 7, an exemplary embodiment of fuzzy set comparison 700 is illustrated. A first fuzzy set 704 may be represented, without limitation, according to a first membership function 708 representing a probability that an input falling on a first range of values 712 is a member of the first fuzzy set 704, where the first membership function 708 has values on a range of probabilities such as without limitation the interval [0,1], and an area beneath the first membership function 708 may represent a set of values within first fuzzy set 704. Although first range of values 712 is illustrated for clarity in this exemplary depiction as a range on a single number line or axis, first range of values 712 may be defined on two or more dimensions, representing, for instance, a Cartesian product between a plurality of ranges, curves, axes, spaces, dimensions, or the like. First membership function 708 may include any suitable function mapping first range 712 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}(\frac{x-c}{\sigma})^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 7, first fuzzy set 704 may represent any value or combination of values as described above, including output from one or more machine-learning models and condition datum determined from biological samples from sensor 108, a predetermined class, such as without limitation previous user data. A second fuzzy set 716, which may represent any value which may be represented by first fuzzy set 704, may be defined by a second membership function 720 on a second range 724; second range 724 may be identical and/or overlap with first range 712 and/or may be combined with first range via Cartesian product or the like to generate a mapping permitting evaluation overlap of first fuzzy set 704 and second fuzzy set 716. Where first fuzzy set 704 and second fuzzy set 716 have a region 728 that overlaps, first membership function 708 and second membership function 720 may intersect at a point 732 representing a probability, as defined on probability interval, of a match between first fuzzy set 704 and second fuzzy set 716. Alternatively, or additionally, a single value of first and/or second fuzzy set may be located at a locus 736 on first range 712 and/or second range 724, where a probability of membership may be taken by evaluation of first membership function 708 and/or second membership function 720 at that range point. A probability at 728 and/or 732 may be compared to a threshold 740 to determine whether a positive match is indicated. Threshold 740 may, in a non-limiting example, represent a degree of match between first fuzzy set 704 and second fuzzy set 716, and/or single values therein with each other or with either set, which is sufficient for purposes of the matching process; for instance, threshold may indicate a sufficient degree of overlap between an output from one or more machine-learning models and/or a condition datum and a predetermined class, such as without limitation a user state, for combination to occur as described above. Alternatively, or additionally, each threshold may be tuned by a machine-learning and/or statistical process, for instance and without limitation as described in further detail below.

Further referring to FIG. 7, in an embodiment, a degree of match between fuzzy sets may be used to classify a condition datum with previous user data. For instance, if a condition datum has a fuzzy set matching element of user data fuzzy set by having a degree of overlap exceeding a threshold, computing device 104 may classify the condition datum as belonging to the element of user data. Where multiple fuzzy matches are performed, degrees of match for each respective fuzzy set may be computed and aggregated through, for instance, addition, averaging, or the like, to determine an overall degree of match.

Still referring to FIG. 7, in an embodiment, a condition datum may be compared to multiple user data fuzzy sets. For instance, condition datum may be represented by a fuzzy set that is compared to each of the multiple element of user data fuzzy sets; and a degree of overlap exceeding a threshold between the condition datum fuzzy set and any of the multiple element of user data fuzzy sets may cause computing device 112 to classify the condition datum as belonging to an element of user data. For instance, in one embodiment there may be two element of user data fuzzy sets, representing respectively a first element of user data and a second element of user data. First element of user data may have a first element of user data fuzzy set; second element of user data may have a second element of user data fuzzy set; and condition datum may have a condition datum fuzzy set. Computing device 112, for example, may compare a condition datum fuzzy set with each of first element of user data fuzzy set and second element of user data fuzzy set, as described above, and classify a condition datum to either, both, or neither of first or second element of user data. Machine-learning methods as described throughout may, in a non-limiting example, generate coefficients used in fuzzy set equations as described above, such as without limitation x, c, and σ of a Gaussian set as described above, as outputs of machine-learning methods. Likewise, condition datum may be used indirectly to determine a fuzzy set, as condition datum fuzzy set may be derived from outputs of one or more machine-learning models that take the condition datum directly or indirectly as inputs.

Figure 8:
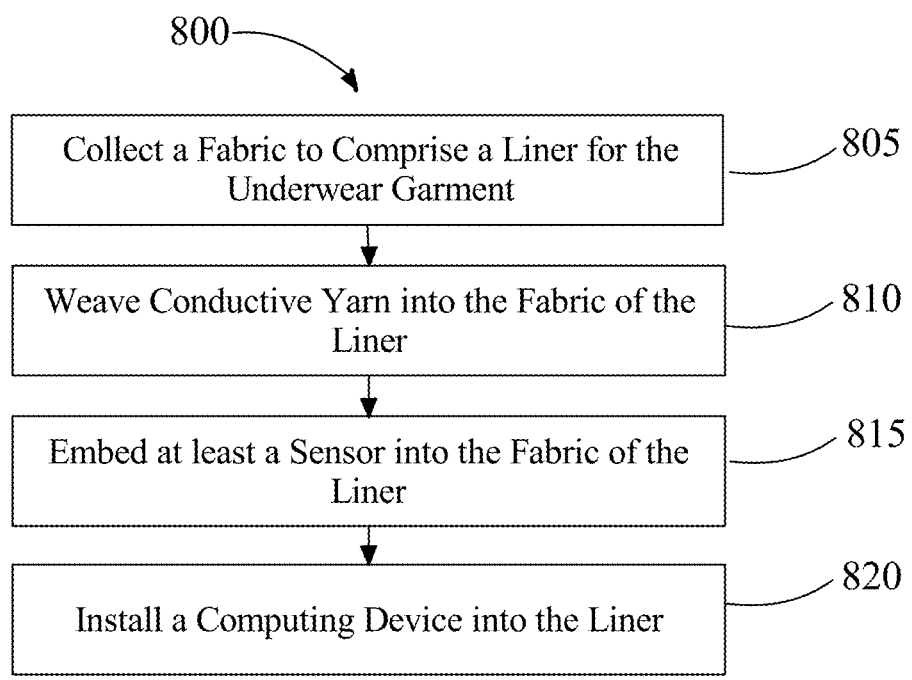
FIG. 8 is a flow diagram illustrating an exemplary embodiment of a method of manufacturing for a garment embedded secretion analysis system.

Now referring to FIG. 8, a flow diagram illustrating an exemplary embodiment of a method 800 of manufacturing for a garment embedded secretion analysis apparatus 100. Garment embedded secretion analysis apparatus 100 may be configured to be worn on a body of a user. At step 805, method 800 includes collecting a fabric to comprise a liner 104 for the garment. Liner 104 may comprise an absorbent material to capture bodily fluids. Fabric may include cotton, polyester, polyamide, elastane, or any of the materials described herein. Fabric of the liner may be a different or the same material used for other aspects of garment embedded secretion analysis apparatus 100. Fabric may be any of the fabric as described herein with reference to FIG. 1. Liner 104 is any of the liners as described herein with reference to FIGS. 1, 2A, 2B, 2C and 2D.

Referring still to FIG. 8, at step 810, method 800 includes weaving conductive yarn into the fabric of the liner 104. As used herein, "conductive yarn" spun thread that is able to conduct an electrical current. Conductive yarn may be woven, or interlaced, into liner 104 using a plain weave, basket weave, twill weave, satin weave, or any other method of connecting fabric together. Conductive yarn may be used to help alleviate or dissipate static electricity or friction between the garment and the kin of the user or other garments. Furthermore, conductive yarn includes a conductive polymer. As used herein, a "conductive polymer" is a substance or material consisting of very large molecules that can conduct an electrical current. Conductive polymers may include, without limitation, polyacetylene (PA), polyaniline (PANT), polypyrrole (PPy), polythiophene (PTH), poly (para-phenylene) (PPP), poly(phenylenevinylene) (PPV), and polyfuran (PF). In one embodiment, method 700 may include weaving a yarn-shaped battery into the fabric of the liner. In a further embodiment, the yarn-shaped battery may be a lithium-ion battery. Conductive yarn may be any of the conductive yarns or fabrics as described herein throughout. Liner 104 is any of the liners as described herein with reference to FIGS. 1, 2A, 2B, 2C, and 2D.

Still referring to FIG. 8, at step 815, method 800 includes embedding at least a sensor 108 into the fabric of the liner 104. As used herein, "embedding" means to fix firmly and deeply in a surrounding mass, which in this case is liner 104. Embedding may involve communicatively connecting. At least a sensor 108 may be any sensor as described herein with reference to FIGS. 1 and 2D. Liner 108 is any of the liners as described herein with reference to FIGS. 1, 2A, 2B, 2C and 2D.

Continuing to refer to FIG. 8, at step 820, method 800 includes installing a computing device 112 into the liner 104. As used herein, "installing" refers to fixing something so it is ready for use. Computing device 112 and/or detection module 116 is configured to measure body temperature. Computing device 112 and/or detection module 116 may be configured to measure a property of a bodily fluid. Property of a bodily fluid may include the presence of a date rape drug in a body of a user. Computing device 112 may include a global positioning system. Computing device 112 may include an activation device, and the activation device may be activated by a biometric authentication. Computing device 112 may include a GPS location feature. Computing device 112 includes a communication protocol. Computing device 112 and/or safety module 128 may be enabled to contact emergency services in case of a threat to a user. Installing a computing device into the fabric of the liner includes embedding wires from these devices into the liner to make them invisible to the user. Computing device 112 may include any of the detection devices as described herein with reference to FIGS. 1 and 2D. Liner 104 is any of the liners as described herein with reference to FIGS. 1, 2A, 2B, 2C and 2D.

Still referring to FIG. 8, method of manufacturing 800 may further include sewing the fabric of the liner to the fabric of the garment. Once all component needed are embedded and installed into liner 104, it may need to be attached to another piece of fabric comprising the rest of the garment. Liner 104 is any of the liners as described herein with reference to FIGS. 1, 2A, 2B, 2C and 2D. Garment embedded secretion analysis apparatus 100 may be any of the systems described herein throughout.

Still referring to FIG. 8, a computing device 112 may be configured to detect a temperature datum using detection module 116 and transmit the temperature datum to the user device 132. Computing device 112 may further be configured to detect a fluid datum using detection module 116 and transmit the fluid datum to the user device 132. Furthermore, computing device 112 may be configured to determine a threat, referred herein as event datum, as a function of the fluid datum, and contact emergency services as a function of the detected threat. Computing device 112 may include data inference engine and reporting engine. Data inference engine may include a machine-learning model trained to correlate a measurement from the detection module to a state of a user. Reporting engine 128 may include a dashboard.

Figure 9:
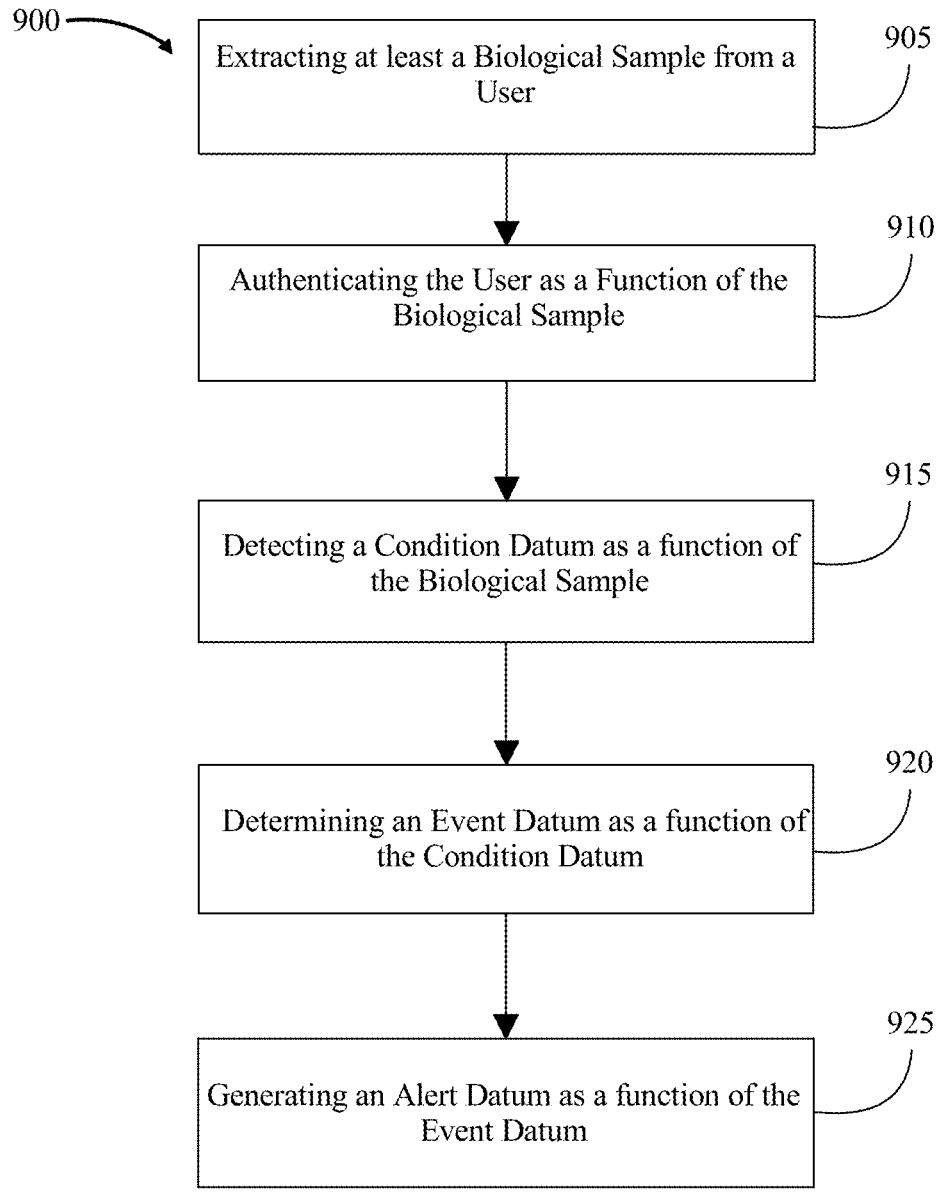
FIG. 9 is a flow diagram illustrating a garment embedded secretion analysis method.

Now referring to FIG. 9, flow diagram illustrating a garment embedded secretion analysis method 900 is presented. At step 905, method 900 includes extracting at least a biological sample from a user. In an embodiment, extraction may refer to the passive collection of biological sample 120 by at least a sensor 108, such as the direct contact with user's skin or sweat particles. In an embodiment, extraction may refer to the collection of biological sample 120 by absorption of sweat or urine particles by liner 104. This step may be implemented as disclosed with reference to FIGS. 1-7.

Continuing to refer to FIG. 9, at step 910, method 900 includes authenticating the user as a function of the at least a biological sample. In an embodiment, authentication may include biological authentication, where biological sample 120 of user is compared to biological data 124, such as a biological sample database 300, associated with the user. In a nonlimiting example, DNA sequence present in biological sample 120 may be compared to DNA sequence of the user in biological data 124, where the user may be authenticated if the DNA sequences are a match. Step 910 may be implemented as disclosed with reference to FIGS. 1-7.

Still referring to FIG. 9, at step 915, method 900 includes detecting a condition datum as a function of the at least a biological sample. In an embodiment, detection module 116 may detect a condition for the user based on the biological sample 120 by comparing the sample to biological data 124 belonging to the user, such as detecting low glucose levels in biological sample 120 for a diabetic user, which detection module 116 would detect a low glucose condition datum. This step may be implemented as disclosed with reference to FIGS. 1-7.

With continued reference to FIG. 9, at step 920, method 900 includes determining an event datum as a function of the condition datum. In an embodiment, detection module 116 may transmit event datum to a user device 132. In a nonlimiting example, an event datum describing a spike in body temperature may not rise to the level where an alert datum would be generated, however user may still want to receive that information in a user device, such as a smartwatch. Step 920 may be implemented as disclosed with reference to FIGS. 1-7.

Still referring to FIG. 9, at step 925, method 900 includes generating an alert datum as a function of the event datum. In an embodiment, alert datum may be generated and transmitted to a user device as a function of an activation device, such as a user pushing a button. In another embodiment, activation device may be activated through a user's movement, such as a specific set of motions. In embodiments, alert datum may include the users GPS location. In a nonlimiting example, a user may feel unsafe and may not have want to bring attention of a possible attacker by pulling out a phone, in that situation user may press a button on activation device embedded in a piece of user's clothes, such as a t-shirt, which may cause safety module 128 to generate an alert with user's GPS location and send it to emergency services, or a user device in user's emergency contact list. In an embodiment, safety module 128 may transmit an alert datum to user's device. In an embodiment, safety module 128 may transmit alert datum to a second user device. In embodiments, safety module 128 may transmit alert datum to user's device and to a second user device. This step may be implemented as disclosed with reference to FIGS. 1-7.

Continuing to refer to FIG. 9. In an embodiment, method 900 may further include transmitting the event datum to a user device. In a nonlimiting example, detection module 116 may determine that biological sample 120 contains low level of glucose and may transmit the low glucose level to a user device, such as a smartwatch worn by the user. In another embodiment, detection modules 116 may determine a condition datum that describes the presence of a drug commonly known as a rape drug, safety module 128 may then generate an alert datum describing the possible involuntary intoxication and may further send an alert to a user device belonging to the user, and another user device associated with an emergency contact for the user and/or emergency services, such as a 911 operator.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
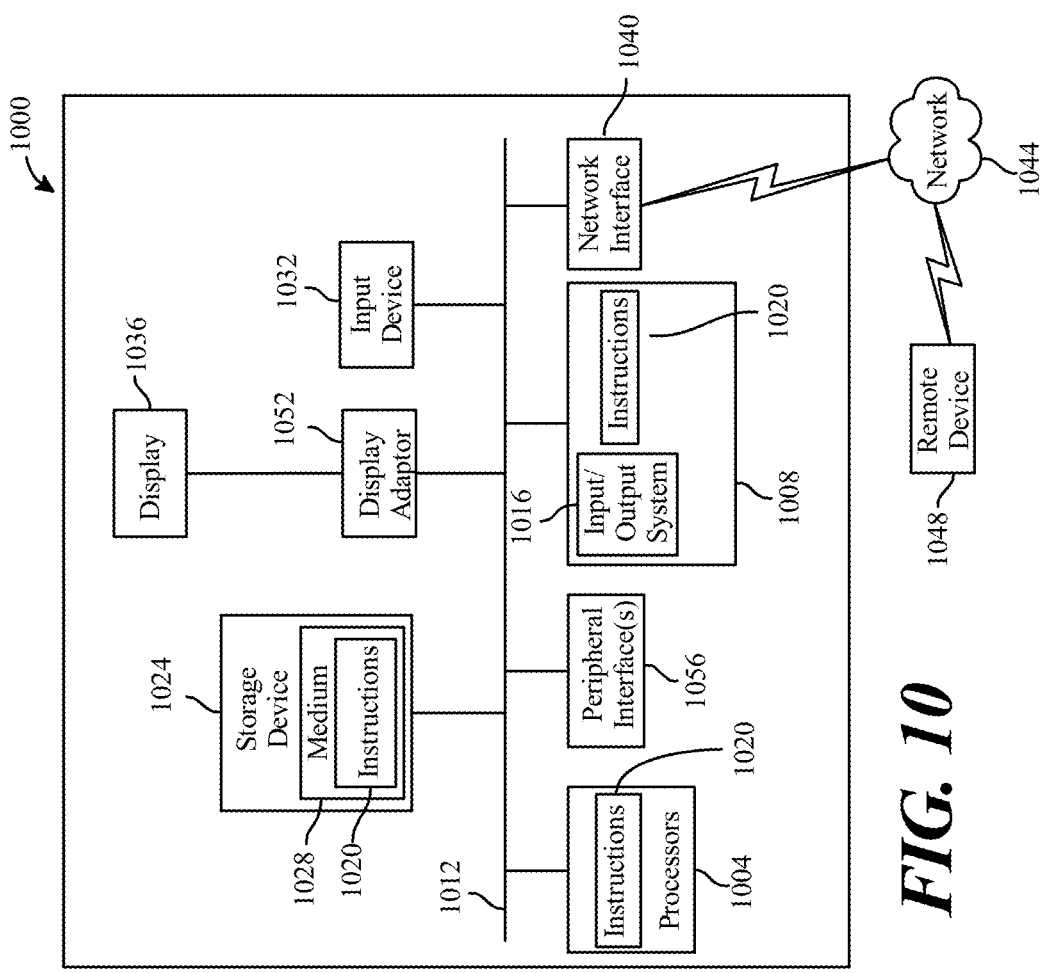
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for a garment embedded secretion analysis, the apparatus comprising:
   a liner comprising at least a sensor from a plurality of sensors, wherein the liner is configured to be attached to a garment worn by a user, wherein the at least a sensor is configured to extract at least a biological sample from the user; and
   a computing device embedded in the liner and communicatively connected to the at least a sensor, the computing device comprising:
      a detection module configured to:
         receive the at least a biological sample from the at least a sensor;
         authenticate the user as a function of the at least a biological sample and biological data of the user;
         detect a condition datum as a function of the at least a biological sample and biological data of the user; and
         determine an event datum as a function of the condition datum; and
      a safety module configured to:
         receive the event datum; and
         generate an alert datum as a function of the event datum, wherein the alert datum is classified into an alert category of a plurality of alert categories, wherein each alert category maps to a different level of emergency.

2. The apparatus of claim 1, wherein the computing device is further configured to authenticate the user as a function of a biological authentication.

3. The apparatus of claim 2, wherein the computing device is further configured to transmit the alert datum to a user device.

4. The apparatus of claim 3, wherein the computing device is further configured to transmit the alert datum to a second user device.

5. The apparatus of claim 2, wherein the alert datum is transmitted as a function of a reporting engine.

6. The apparatus of claim 4, wherein the second user device is an emergency service.

7. The apparatus of claim 1, wherein the apparatus further comprises a battery embedded in the liner.

8. The apparatus of claim 7, wherein the battery is a yarn-shaped battery.

9. The apparatus of claim 1, wherein the liner comprises an absorbent material.

10. The apparatus of claim 1, wherein the at least a sensor comprises a sensor configured to measure body temperature.

11. The apparatus of claim 1, wherein the computing device further comprises a global positioning system (GPS).

12. The apparatus of claim 11, wherein the alert datum comprises the user's GPS location.

13. The apparatus of claim 1, wherein the safety module is further configured to generate the alert datum as a function of a user motion.

14. A method for a garment embedded secretion analysis, the method comprising:
   extracting, by a computing device communicatively connected to at least a sensor embedded in a liner, at least a biological sample from a user;
   authenticating, by the computing device, the user as a function of the biological sample and biological data of the user;
   detecting, by the computing device, a condition datum as a function of the biological sample and biological data of the user;
   determining, by the computing device, an event datum as a function of the condition datum; and
   generating, by the computing device, an alert datum as a function of the event datum, wherein the alert datum is classified into an alert category of a plurality of alert categories, wherein each alert category maps to a different level of emergency.

15. The method of claim 14, wherein the method further comprises transmitting, by the computing device, the event datum to a user device.

16. The method of claim 15, wherein the method further comprises transmitting, by the computing device, the alert datum to the user device.

17. The method of claim 16, wherein the method further comprises transmitting the alert datum to a second user device.

18. The method of claim 14, wherein the alert datum comprises a GPS location of the user.

19. A method of manufacturing a garment embedded secretion analysis system, wherein the method of manufacturing comprises:
   collecting a fabric to comprise a liner for the garment;
   weaving conductive yarn into the fabric of the liner;
   embedding at least a sensor from a plurality of sensors into the fabric of the liner, wherein the at least a sensor is configured to extract at least a biological sample from a user of the garment; and
   installing a computing device into the liner, wherein:
      the computing device is configured to generate an alert datum as a function of the at least a biological sample;
      the alert datum is classified into an alert category of a plurality of alert categories; and each alert category maps to a different level of emergency.

20. The method of claim 19, wherein the method further comprises weaving a yarn-shaped battery into the fabric of the liner.

* * * * *